(12) United States Patent
Sharma et al.

(10) Patent No.: US 10,946,113 B2
(45) Date of Patent: Mar. 16, 2021

(54) APPARATUS AND SYSTEM FOR AIR CLEANING

(71) Applicant: VBreathe Pty Ltd, Newcastle (AU)

(72) Inventors: Mohit Sharma, Pyrmont (AU); Robert Brian Seaman, Balmain (AU); Abigail Maude Thomas, Balmain (AU)

(73) Assignee: VBREATHE PTY LTD, Prymont (AU)

( * ) Notice: Subject to any disclaimer, the term of this patent is extended or adjusted under 35 U.S.C. 154(b) by 0 days.

(21) Appl. No.: 16/471,133

(22) PCT Filed: Oct. 25, 2017

(86) PCT No.: PCT/AU2017/051174
§ 371 (c)(1),
(2) Date: Jun. 19, 2019

(87) PCT Pub. No.: WO2018/112507
PCT Pub. Date: Jun. 28, 2018

(65) Prior Publication Data
US 2020/0038541 A1 Feb. 6, 2020

(30) Foreign Application Priority Data

Dec. 22, 2016 (AU) .............................. 2016905336
May 17, 2017 (AU) .............................. 2017901850

(51) Int. Cl.
*A61L 9/12* (2006.01)
*A61L 9/04* (2006.01)
(Continued)

(52) U.S. Cl.
CPC .............. *A61L 9/122* (2013.01); *A61L 9/048* (2013.01); *F24F 11/39* (2018.01); *F24F 11/58* (2018.01);
(Continued)

(58) Field of Classification Search
None
See application file for complete search history.

(56) References Cited

U.S. PATENT DOCUMENTS 3,096,817 A   7/1963   Mckenna
3,633,881 A   1/1972   Yurdin
(Continued)

FOREIGN PATENT DOCUMENTS

CN      107327966 A   *   11/2017
JP      2015097695 A       5/2015

OTHER PUBLICATIONS

Wang et al. CN107327966A—translated document (Year: 2017).*

*Primary Examiner* — Jelitza M Perez
(74) *Attorney, Agent, or Firm* — Oppenhuizen Law PLC; David L. Oppenhuizen

(57) ABSTRACT

An air filtering and treatment apparatus (10), the apparatus (10) including: a housing (12) having an air inlet (14), an air outlet (16), an air passageway (24) between the inlet (14) and outlet (16), and a fan (18) arranged to urge air through the air passageway (24) between the air inlet (14) and the air outlet (16), wherein the housing (12) includes filter (20) arranged to filter air passing through the air passageway (24), and a receptacle (26) located toward the air outlet (16) relative to filter (20). The receptacle (26) is adapted to hold treatment composition (22) such that an evaporable vapour associated with the treatment composition (22) is able to accumulate in a headspace (41) of the receptacle (26), the headspace (41) including at least one aperture (36). The air passageway (24) may be shaped such that air flows substantially perpendicularly past the at least one aperture (36) of the receptacle (26) such that a pre-determined amount of the evaporable vapour is entrained into the filtered air released from the air outlet (16). A system (100) and method are also disclosed.

17 Claims, 12 Drawing Sheets

(51) Int. Cl.
*F24F 11/39* (2018.01)
*F24F 11/58* (2018.01)
*F24F 110/20* (2018.01)
*F24F 110/64* (2018.01)
*F24F 110/10* (2018.01)
*F24F 3/16* (2021.01)

(52) U.S. Cl.
CPC ..... *A61L 2209/133* (2013.01); *A61L 2209/14* (2013.01); *F24F 2003/1675* (2013.01); *F24F 2110/10* (2018.01); *F24F 2110/20* (2018.01); *F24F 2110/64* (2018.01)

(56) References Cited

U.S. PATENT DOCUMENTS

| | | | | |
|---|---|---|---|---|
| 3,990,848 | A | * | 11/1976 | Corris ................ A61L 9/122 422/49 |
| 4,743,406 | A | | 5/1988 | Steiner et al. |
| 5,935,526 | A | * | 8/1999 | Moore ................ A61L 9/122 239/56 |
| 6,363,734 | B1 | * | 4/2002 | Aoyagi ................ A61L 2/10 62/264 |
| 2005/0284168 | A1 | * | 12/2005 | Lee ................ F24F 1/0007 62/317 |
| 2008/0019861 | A1 | | 1/2008 | Silderhuis |
| 2011/0126713 | A1 | * | 6/2011 | Legare ............ B01D 46/521 96/135 |

\* cited by examiner

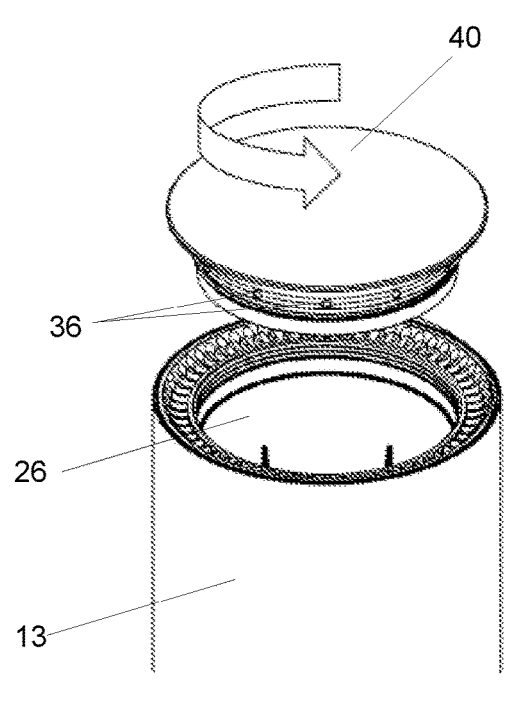
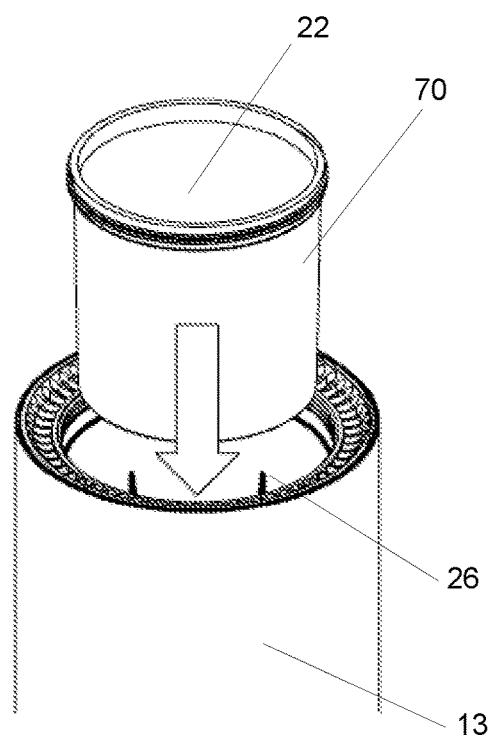
Figure 12a
Figure 12b
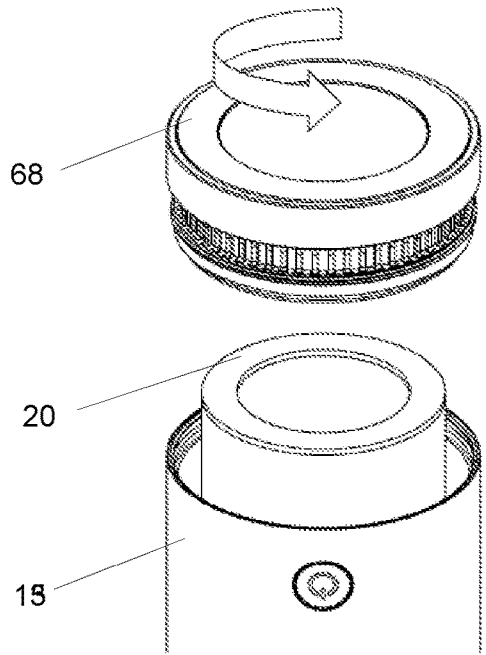
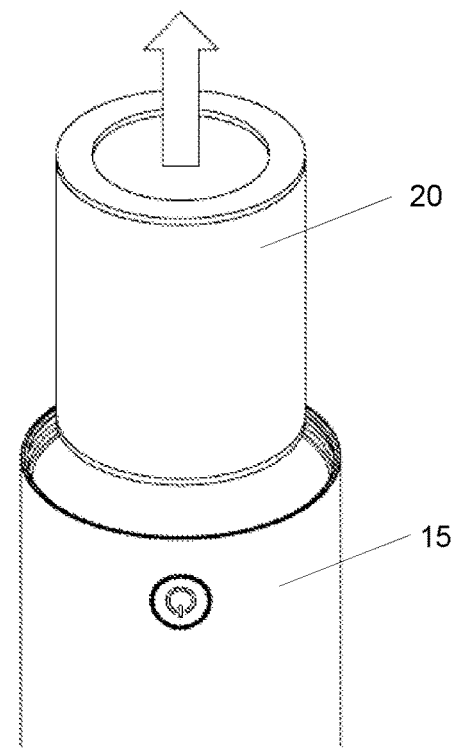
Figure 13a
Figure 13b

APPARATUS AND SYSTEM FOR AIR CLEANING

RELATED APPLICATIONS

This application is a National Stage of International Application No. PCT/AU2017/051174, filed Oct. 25, 2017, which claims priority from Australian Provisional Patent Nos. 2016905336 filed Dec. 22, 2016, and 2017901850 filed May 17, 2017, the contents of which are incorporated by reference in their entirety.

TECHNICAL FIELD

The invention relates to an apparatus and system for air cleaning, in particular, the filtering and treating or sanitising of indoor air.

BACKGROUND

Air quality, in particular, indoor air quality may be compromised by the presence of dust, pet dander, odours, airborne organic matter such as mould and airborne pathogens. Accordingly, various types of indoor air filtering devices have been proposed.

One such air-filtering device includes a housing having a fan that draws air through the rear centre of the unit, passes the air through a filter and then discharges the air through a grille at the top of the housing. The filter may be a HEPA (High Efficiency Particulate Air) filter that is arranged to collect microscopic particles such as allergy-provoking pollen grains, dust mites, mould spores and pet dander particles. An ioniser may also be included.

A problem with these devices is that the device cleans only the air that is drawn into the housing and through the filter. Another problem is that the filtering of the air may not remove and kill some microscopic particles such as dust mites and mould spores.

Other such air-filtering devices may include aromatic or disinfectant substances that are emitted from the air-filtering device into the filter air stream.

However, a problem with such air-filtering devices relates to the longevity and efficacy of the air freshening or disinfectant substances, and ease of use for a user to, for example, replenish the substance. A further problem relates to the control of the release of the substance, and such air-filtering devices may include relatively complex means to control the release of the substance.

The invention disclosed herein seeks to overcome one or more of the above identified problems or at least provide a useful alternative.

SUMMARY

In accordance with a first broad aspect there is provided, an air filtering and treatment apparatus, the apparatus including: a housing having an air inlet, an air outlet, an air passageway between the inlet and outlet, and a fan arranged to urge air through the air passageway between the air inlet and the air outlet, wherein the housing includes filter arranged to filter air passing through the air passageway, and a receptacle located toward the air outlet relative to filter, wherein the receptacle is adapted to hold treatment composition such that an evaporable vapour associated with the treatment composition is able to accumulate in a headspace of the receptacle, the headspace including at least one aperture located at a side thereof, and wherein a portions of the air passageway, that may be an outlet portion, is shaped such that air flows substantially perpendicularly past the at least one aperture of the receptacle such that a pre-determined amount of the evaporable vapour is entrained into the filtered air released from the air outlet.

In an aspect, the receptacle is adapted to received a removable cartridge containing the treatment composition, the cartridge terminating short of the at least one aperture so as to allow fluid communication between the treatment composition and the least one aperture.

In another aspect, the receptacle includes a lid removeably securable thereto.

In yet another aspect, the lid includes a head and a neck, and wherein the neck provides the side of the headspace and includes the at least one aperture.

In yet another aspect, the head includes radial lip extending at least partially over the air outlet so as to outwardly deflect airflow.

In yet another aspect, the radial lip is located immediately above the at least one aperture, and wherein the at least one aperture is located at the air outlet.

In yet another aspect, the outlet portion of the air passageway is arranged to be normally vertically oriented.

In yet another aspect, the at least one aperture substantially skirts the side of headspace.

In yet another aspect, the at least one aperture is provided in the form of a plurality of space apart apertures substantially skirting the side of headspace.

In yet another aspect, the outlet portion of the air passageway substantially skirts the headspace and the apertures.

In yet another aspect, the at least one aperture is provided in the form of a plurality of radially arranged apertures spaced apart and substantially skirting the side of headspace, and wherein the outlet portion of the air passageway is annular in shape and substantially skirts the plurality of radially arranged apertures.

In yet another aspect, the at least one aperture is arranged at the air outlet.

In yet another aspect, a size of the at least one aperture is selected such that the pre-determined amount of the evaporable vapour is in range of about 0.5 to 2.5 grams per day, and preferably about 1 gram per day.

In yet another aspect, the size of the at least one aperture is selected such that the pre-determined amount of the evaporable vapour is in range of about 0.5 to 2.5 grams per day with an airflow rate through the air passageway in the range of about 4 to 8 litres per second.

In yet another aspect, the housing includes a base and a top, and wherein the air inlet is located toward the base and the air outlet is located toward the top.

In yet another aspect, the at least one aperture is provided in the form of a plurality of apertures arranged toward a top of the receptacle, the plurality of apertures being arranged perpendicular to the direction of the air directed by the outlet portion of the air passageway.

In yet another aspect, the outlet portion of the passageway is annular in shape being defined between an outer wall of the housing and the receptacle.

In yet another aspect, the receptacle includes an associated removable lid shaped to cover the receptacle, the lid including a head and a neck, the neck including the plurality of apertures.

In yet another aspect, the head of the lid is arranged to deflect air directed by the passageway at least partially laterally of the housing.

In yet another aspect, the neck of the lid is received at least partially within a rim of the outer wall of the housing, the width of the outlet being defined between the neck and the rim of the outer wall of the housing.

In yet another aspect, the lid is removable to access the receptacle.

In yet another aspect, the filter is located within a bottom portion of the housing toward the base and the receptacle is located in an upper portion of the housing toward the top.

In yet another aspect, the base is removable to change the filter.

In yet another aspect, the fan is controllable via a controller.

In yet another aspect, the housing includes a particle sensor and a conduit to communicate environmental air with the particle sensor, the particle sensor being in communication with the controller such that the fan is controllable in response to the particle level detected by the particle sensor.

In yet another aspect, the apparatus includes a further fan adapted to circulate environmental air to the particle sensor.

In yet another aspect, the apparatus includes an indicator light in communication with the controller, the indicator light being selectively illuminated by the controller to indicate a quality of the air as detected by particle sensor.

In yet another aspect, the housing contains the controller, a battery in communication with the controller and at least one user control.

In yet another aspect, the controller is adapted to communicate with a remote device.

In yet another aspect, the treatment composition is adapted to effect or kill air born pathological or biological material.

In yet another aspect, the apparatus includes a substantially sealed inner electronics housing located within the housing, the inner housing being located between the fan and the receptacle, and being shaped to direct air from the fan to the outlet portion of the air passageway.

In accordance with a second broad aspect there is provided, a system including an apparatus as defined in any one of the previous claims and a remote device adapted to communicate with and operate the device.

In an aspect, the system includes a controller and a sensor in communication with the controller configured to measure at least one of air particles and a dew point of the surrounding air environment, and provide a user prompt if the least one of the air particles and the dew point exceed a predetermined threshold.

In an aspect, the system includes a controller and a sensor in communication with the controller configured to measure at least one of particles and a dew point of the surrounding air environment, and automatically activate the fan of the apparatus if at least one or the particles and the dew point levels exceed a predetermined threshold.

In another aspect, the system includes a controller and a sensor in communication with the controller configured to measure at least one of particles and a dew point of the surrounding air environment, and automatically increase the fan speed of the apparatus if at least one of the particles and the dew point levels exceed a predetermined threshold.

In yet another aspect, the at least one of the particle and dew point sensors are carried by the housing of the apparatus.

In accordance with a third broad aspect there is provided, an air filtering and treatment apparatus, the apparatus including: a housing having an air inlet toward a base thereof, an air outlet toward to top thereof, an air passageway between the inlet and outlet, and a fan arranged to urge air through the air passageway between the air inlet and the air outlet, wherein the housing includes filter located toward the base arranged to filter air passing through the air passageway, and a receptacle located toward the air outlet relative to filter, wherein the base is removable to allow changing of the filter, and wherein the receptacle includes a removable lid to allow fitting of a removable cartridge containing a treatment composition to the receptacle such that an evaporable vapour associated with the treatment composition is able to accumulate in a headspace of the receptacle, the headspace including at least one aperture located at a side thereof, and wherein an outlet portion of the air passageway is shaped such that air flows past the at least one aperture of the receptacle such that a rate of the evaporable vapour is entrained into the filtered air released from the air outlet.

In accordance with a fourth broad aspect, an air filtering and treatment apparatus, the apparatus including: a housing having an air inlet toward a base thereof, an air outlet toward to top thereof, an air passageway between the inlet and outlet, and a fan arranged to urge air through the air passageway between the air inlet and the air outlet, wherein the housing includes filter arranged to filter air passing through the air passageway, and a receptacle located toward the air outlet relative to filter, wherein the filter is located toward the base and the base is removable to allow changing of the filter, and wherein the receptacle includes a removable lid to allow fitting of a removable cartridge containing a treatment composition such that a vapour associated with the treatment composition is able to accumulate in the receptacle, the receptacle including at least one aperture adapted to communicate the vapour with filtered air such that emitted air contains a pre-determined amount of the vapour.

In accordance with a fifth broad aspect there is provided, an air filtering and treatment apparatus, the apparatus including: a housing having an air inlet, an air outlet, an air passageway between the inlet and outlet, and a fan arranged to urge air through the air passageway between the air inlet and the air outlet, wherein the housing includes filter arranged to filter air passing through the air passageway, and a receptacle located toward the air outlet relative to filter, wherein the filter is removable to allow changing of the filter, and wherein the receptacle is adapted to receive a removable cartridge containing a treatment composition, the receptacle including at least one aperture adapted to communicate a vapour associated with the treatment composition with filtered air such that emitted air contains a pre-determined amount of the vapour.

In accordance with a sixth broad aspect there is provided, a method for air filtering and treating, the method including: drawing air though a housing using a fan such that air is passed between an inlet and an outlet of the housing; filtering the air using a filter arranged between inlet and the outlet to provide filtered outlet air; and treating the filtered air proximate the outlet by communicating the filtered air with a receptacle containing a treating composition such that a portion of the treating composition is entrained into the filtered outlet air.

In an aspect, the method includes: measuring air quality parameter; and at least one of activating and altering the fan speed based on the measured air quality parameter.

In another aspect, the method includes: measuring an air quality parameter; and providing an air quality alert based on the measured air quality parameter.

BRIEF DESCRIPTION OF THE FIGURES

The invention is described, by way of non-limiting example only, by reference to the accompanying figures, in which:

FIGS. 12a and 12b respectively illustrate perspectives views of a lid of the housing being removed to reveal a receptacle and a sanitising composition being fitted to the receptacle;

FIGS. 13a and 14b respectively illustrate perspective views of a removable base of the housing and a filter being fitted to the base of the housing; and FIG. 14 is a system diagram illustrating the apparatus in communication either directly or indirectly with an external device such as smart phone or the like.

DETAILED DESCRIPTION

Figure 11:
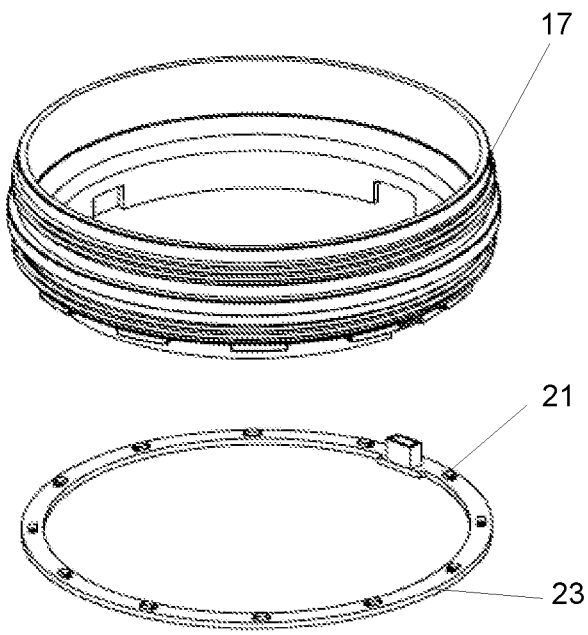
FIG. 11 is an exploded parts front perspective view illustrating an intermediate coupling and light ring of the apparatus.
Figure 14:
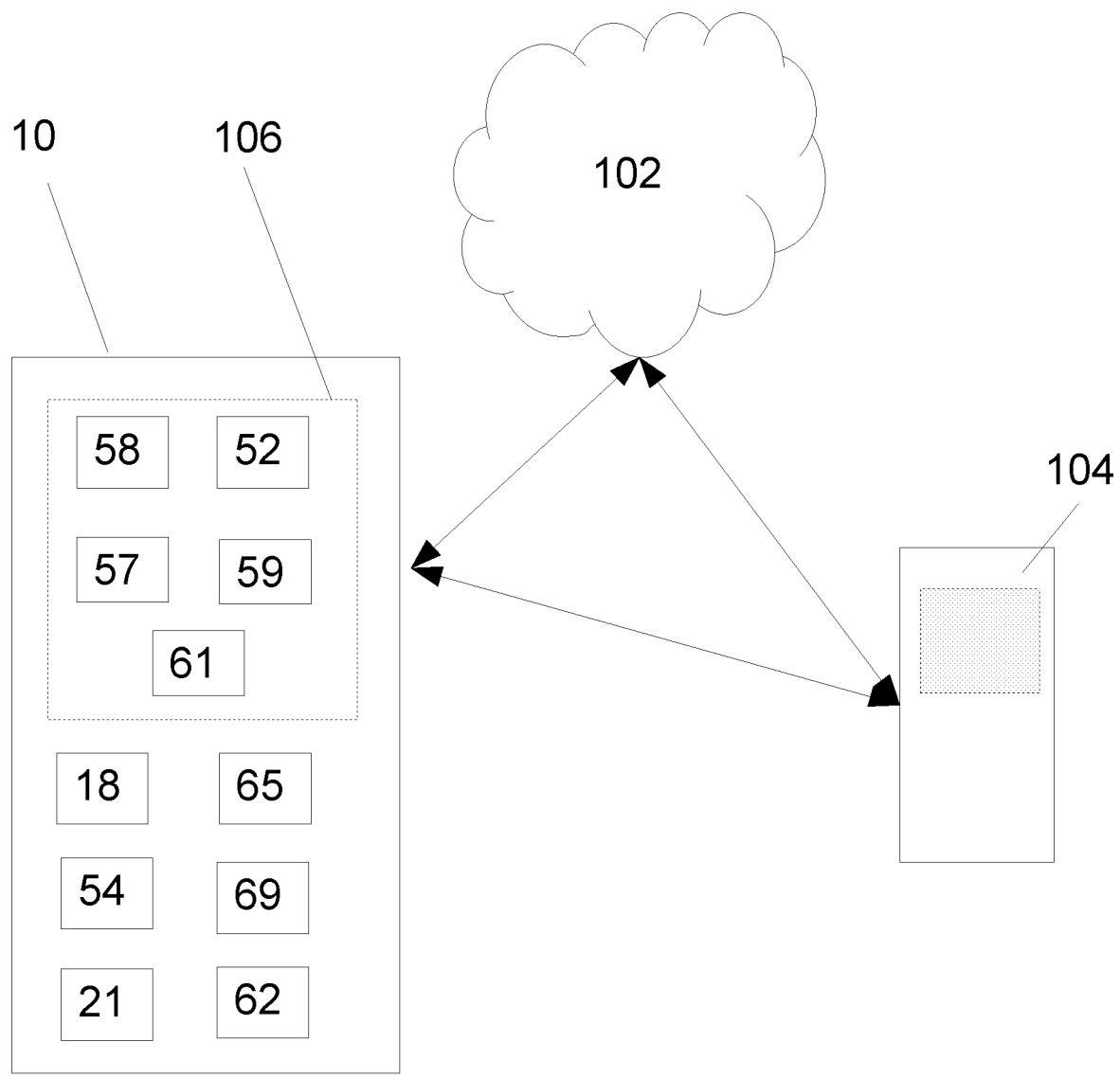

Referring to FIGS. 1 to 7, there is shown an apparatus 10 for the filtering and sanitising of air, in particular, indoor air. The apparatus 10 includes a housing or housing assembly 12 having an air inlet 14, an air outlet 16 and a fan 18 arranged to urge air between the air inlet 14 and the air outlet 16. The housing assembly 12 includes an upper housing 13 and a lower housing 15 that are coupled via an intermediate coupling 17. The intermediate coupling 17, shown best in FIG. 11, supports lights 21 in a ring 23 centrally of the upper and lower housings 13, 15. The lights 21 may be Red, Green Blue (RGB) lights.

The housing 12 includes a filter 20 and a composition 22 arranged between the air inlet 14 and the air outlet 16, the arrangement being such that filtered air is communicated with the composition 22 so as to allow a part or amount of the composition 22 to be entrained into the filtered air released from the air outlet 16. Accordingly, air released by the apparatus 10 has been filtered and also includes a small amount of the composition 22. As is further detailed below, the composition 22 may be an evaporable vapour releasing composition such as gel or gel cartridge impregnated or formulated with essential oils or other suitable substances.

Turning firstly to the apparatus 10 in more detail, the housing 12 includes a base 28, a top 30 and a skirting sidewall 32. The base 28 is fitted with a friction pad 29 to assist with supporting the base 28. The housing 12 defines an air passageway 24 between the air inlet 14 and the air outlet 16, and includes a receptacle 26 to hold or contain the composition 22 and a lower void 34 to hold or locate the filter 20. The air passageway 24 generally directs air from the air inlet 14, through the filter 20 and fan 18, and about the receptacle 26 to the air outlet 16. The housing 12 includes outlet vanes 27 located proximate the outlet 16. In this example, the outlet vanes 27 are supported by the receptacle 26 and extend radially therefrom.

The air inlet 14 is located toward the base 28 and the air outlet 16 is located toward the top 30 so that air is generally drawn from the base 28 of the apparatus 10 and emitted from or toward the top 30 of the apparatus 10. The housing 12 may be generally cylindrical and may be free standing. In this example, the overall size of the housing 12 may be about 90 mm diameter×240 mm high, and therefore be suitable for desktop use. However, other shapes and support configuration are possible and contemplated herein such as square shapes and wall mounted variations.

One or more apertures 36 are provided between the receptacle 26 and air directed by the passageway 24 so as to provide controlled entrainment part or a portion of the composition 22. In more detail, in this example, the receptacle 26 is cylindrical and is spaced apart from the side wall 32 to define an outlet annular portion 38 of the passageway 24 that skirts the receptacle 26 and terminates at the air outlet 16. The annular portion 38 has an area that is about the same as the open area of the fan 18. It is noted that in other examples, the apertures 36 may be located anywhere between the air outlet 16 and the fan 18, and may not always be proximate the air outlet 16.

The receptacle 26 includes an associated removable lid 40. The lid 40 includes a head 42 and a neck 44 extending therefrom. The neck 44 includes a free threaded coupling end 46 and includes the one or more apertures 36 skirting the neck 44 between the free coupling end 46 and the head 42. In this example, the one or more apertures 36 are provided in the form of a ring small radially spaced apart apertures 39 through which part of the composition, such as evaporable or volatile gasses, pass from with the receptacle 26 toward or at the outlet 16. The free coupling end 46 is arranged to rotatably engage with the receptacle 26 and stop with enough clearance so that the one or more apertures 36 are exposed to the air flow.

A rim or lip 48 of the head 42 of the lid 40 is tapered so as to deflect air flowing through the passageway 24 upwardly and partially laterally of the housing 12. It is noted that the one or more apertures 36 are positioned proximate the outlet 16 where expansion takes place to assist to utilise a venturi effect. The one or more apertures 36 are also relatively small to assist to contain the composition 22 and inhibit or reduce evaporation unless air is flowing.

In a fitted condition, the lid 40 is coupled to and received by the receptacle 26 and rim 48 extending radially proud of the receptacle 26 above and at least partially over and above the passageway 24. The apertures 36 on the neck 44 of the lid 40 remain unobstructed to allow fluid communication from receptacle 26. The upper rim 50 of the housing 12 is located below and outwardly of the rim 48 of the lid 40. The lid 40 is removable to access the receptacle 26 and replace the composition 22, as required.

The receptacle 26 is arranged to provide a headspace 41 above the composition 22 to allow for vapour associated with the composition 22 to build or accumulate within the headspace 41. The apertures 36 are located about the headspace 41 to allow for fluid communication of the vapour through the apertures 36 and into the airstream. The neck 44 of the lid 40 provides at least part of the side wall of the headspace 41.

Figure 1:
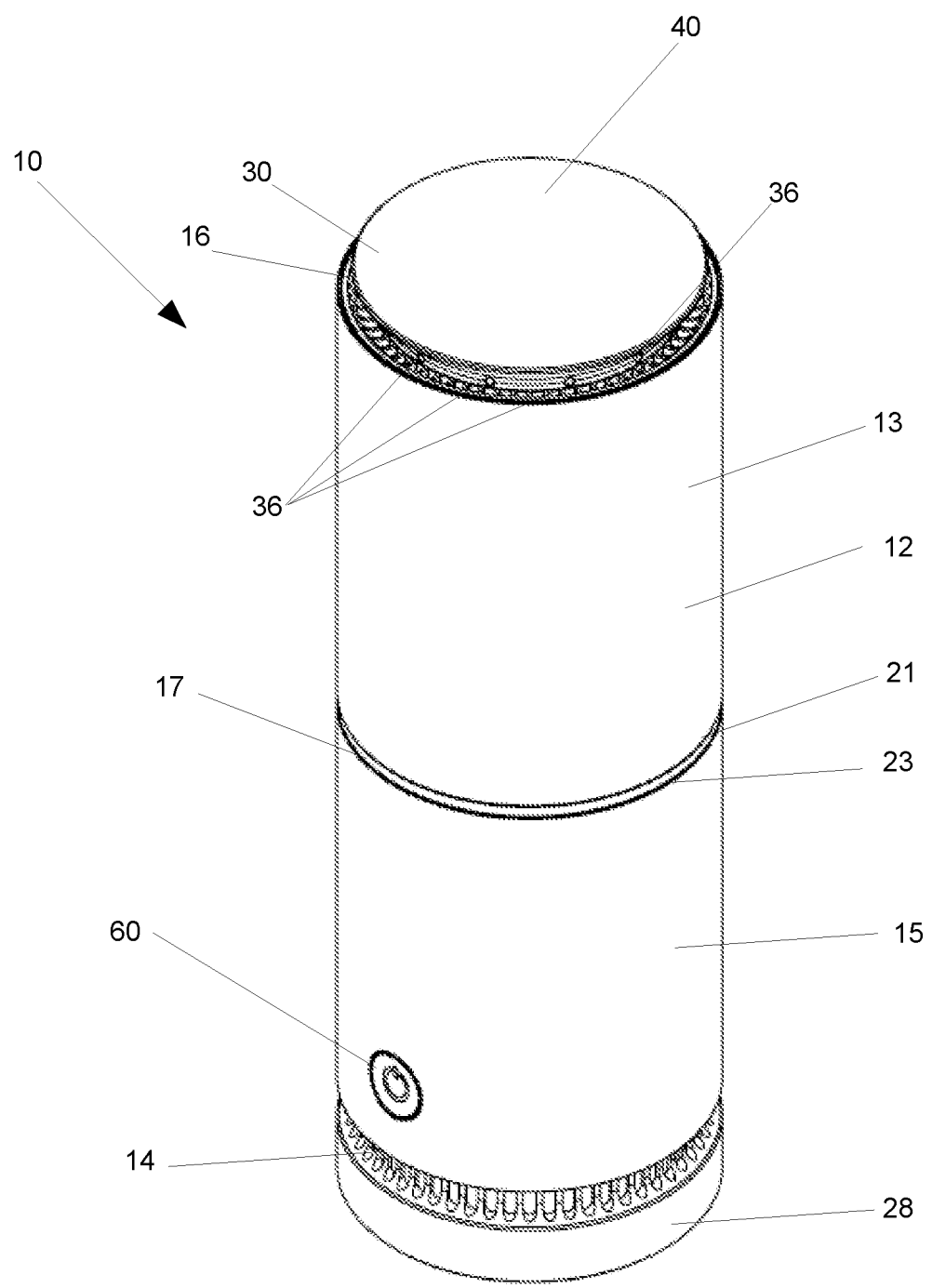
FIG. 1 is a front perspective view illustrating an example of the apparatus.
Figure 2:
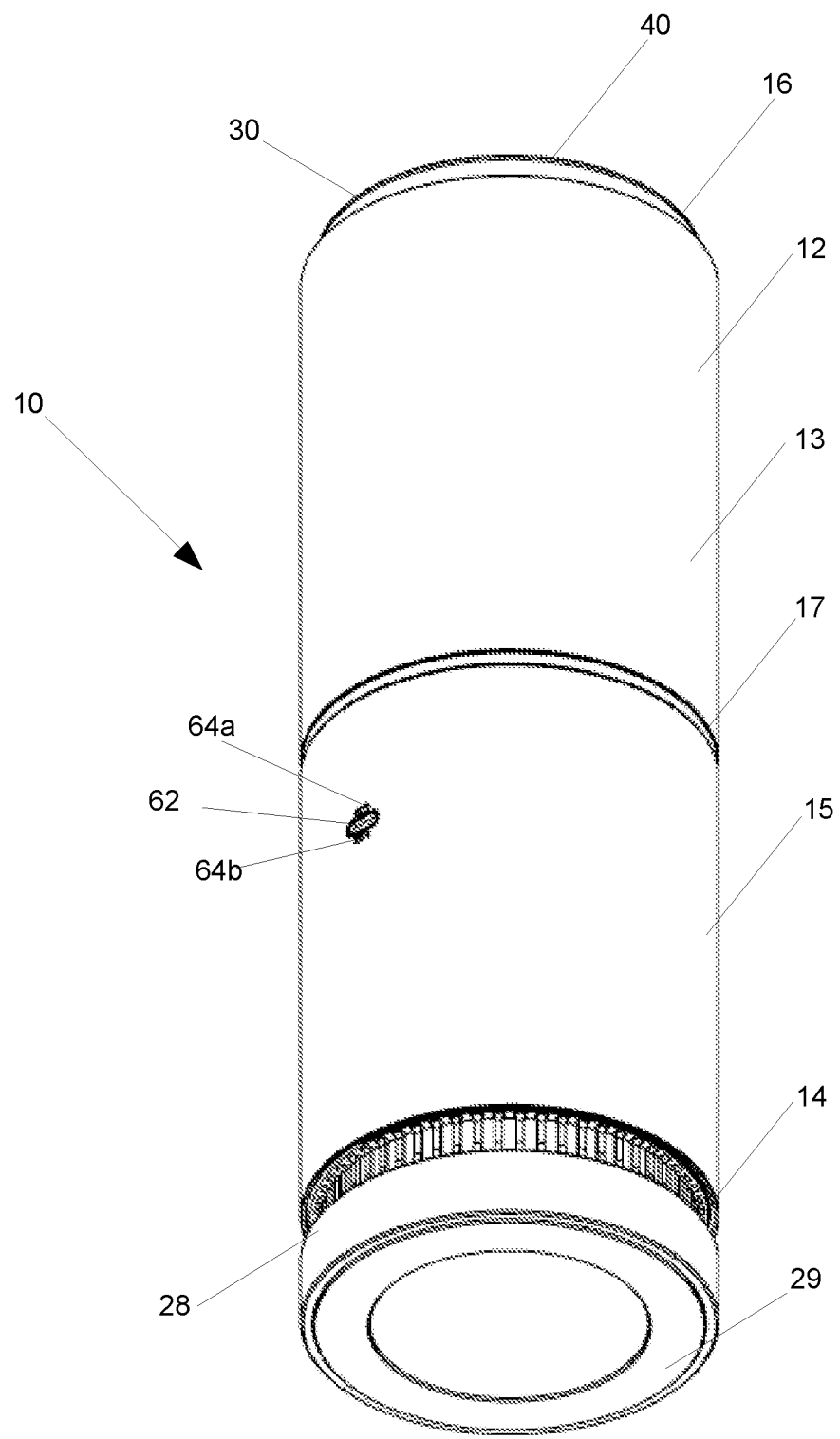
FIG. 2 is a rear perspective view illustrating an example of the apparatus.
Figures 3, 4:
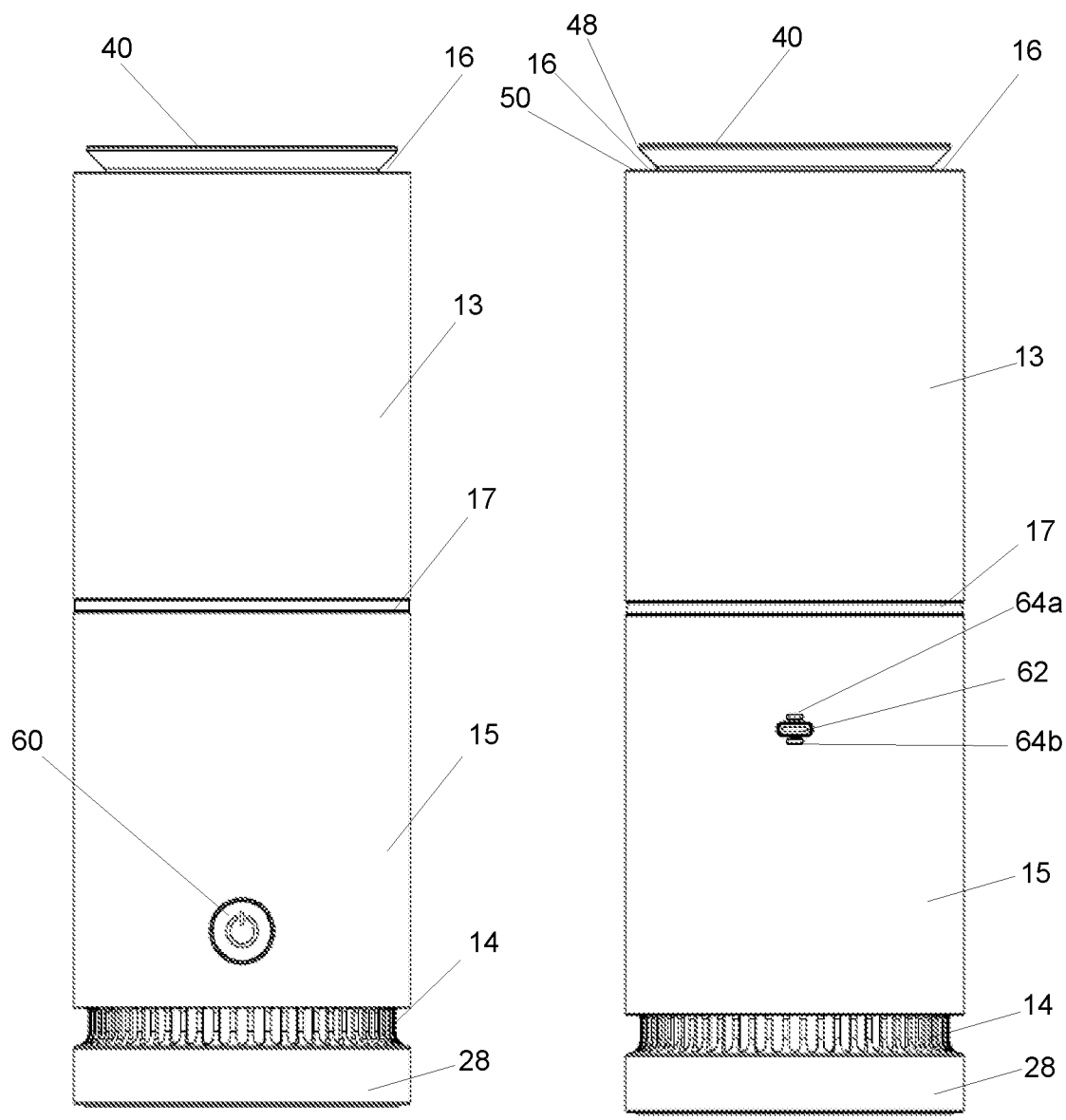
FIG. 3 is a front view illustrating the apparatus.
FIG. 4 is a rear view illustrating the apparatus.
Figure 5:
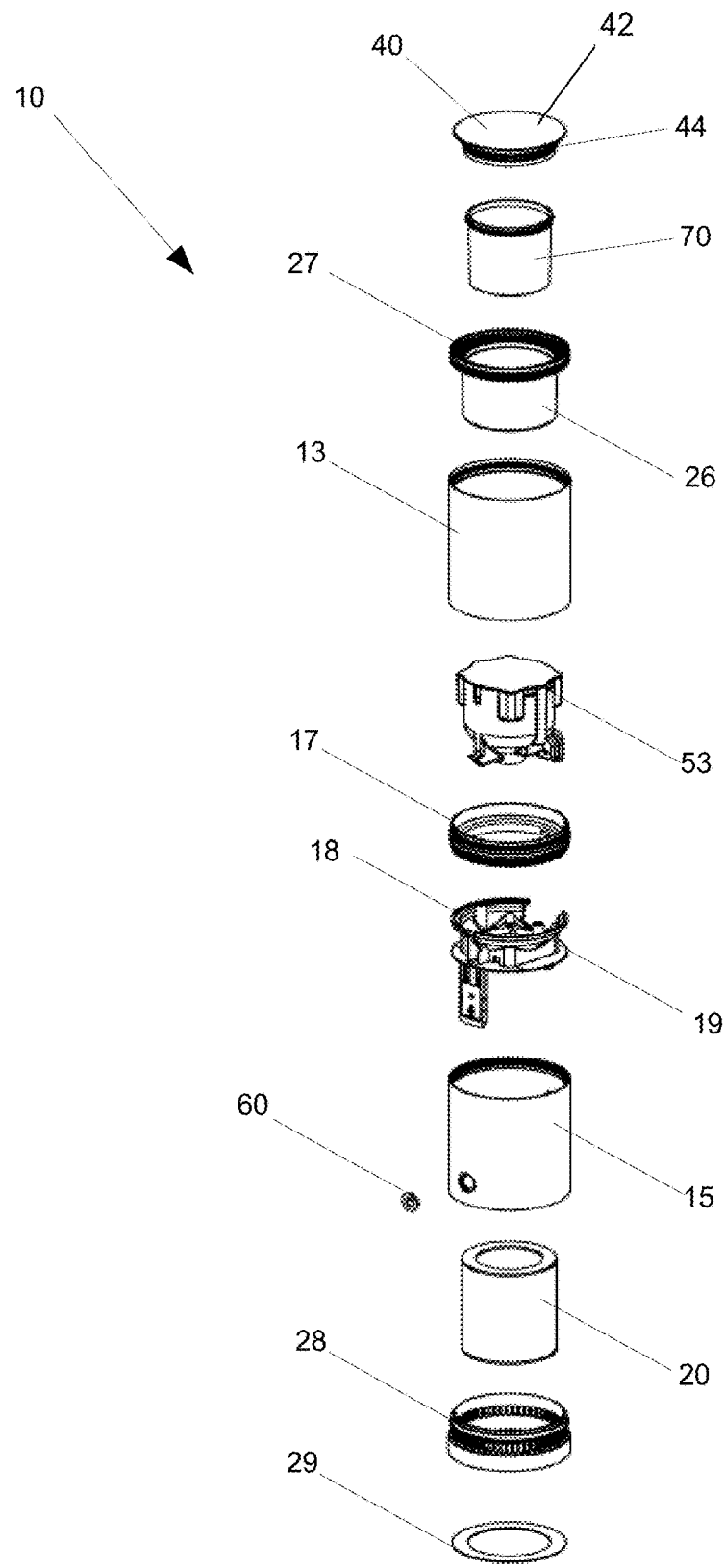
FIG. 5 is an exploded parts front perspective view illustrating the apparatus.
Figure 6:
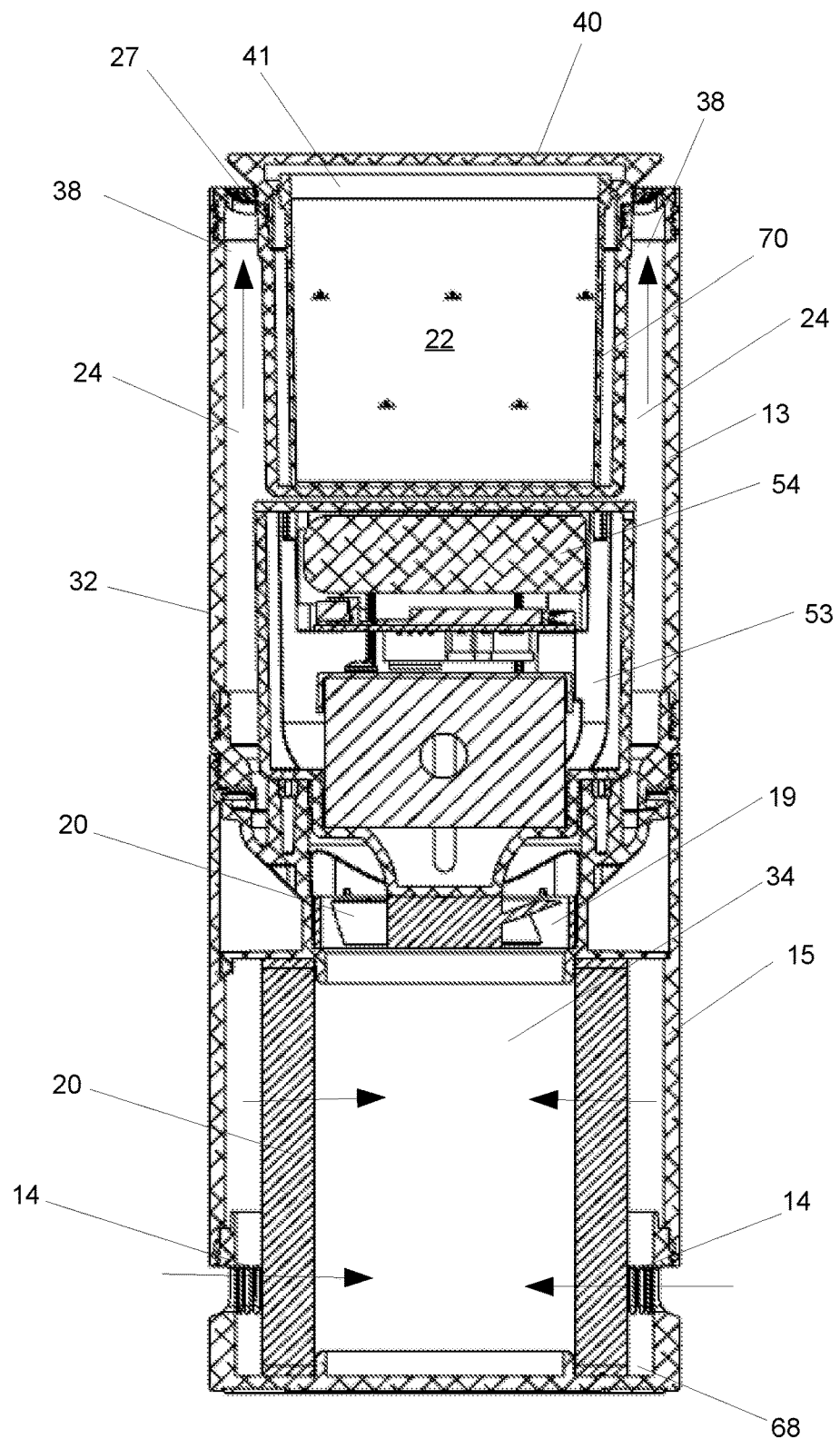
FIG. 6 is a front sectional view illustrating the apparatus.
Figure 7:
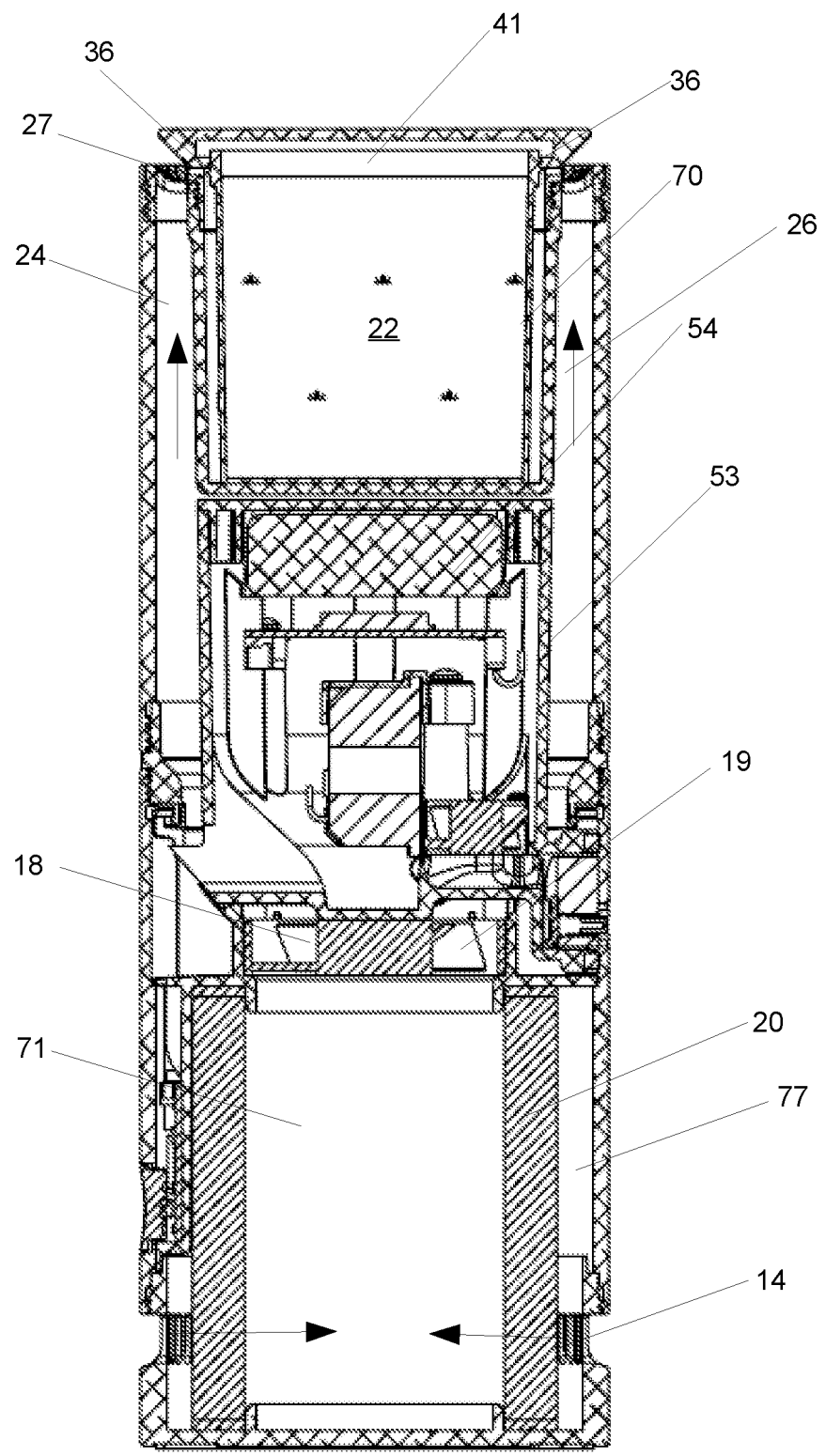
FIG. 7 is a side sectional view illustrating the apparatus.
Figure 8:
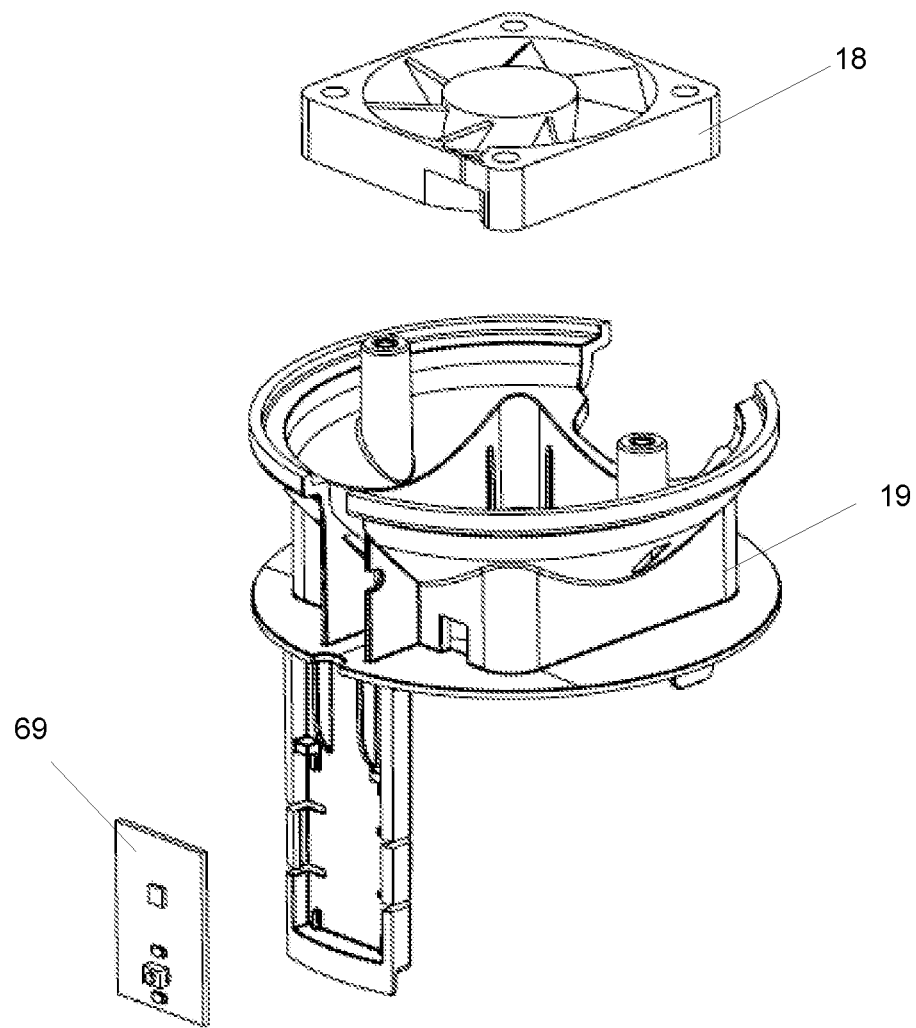
FIG. 8 is an exploded parts front perspective view illustrating the fan housing.
Figure 9:
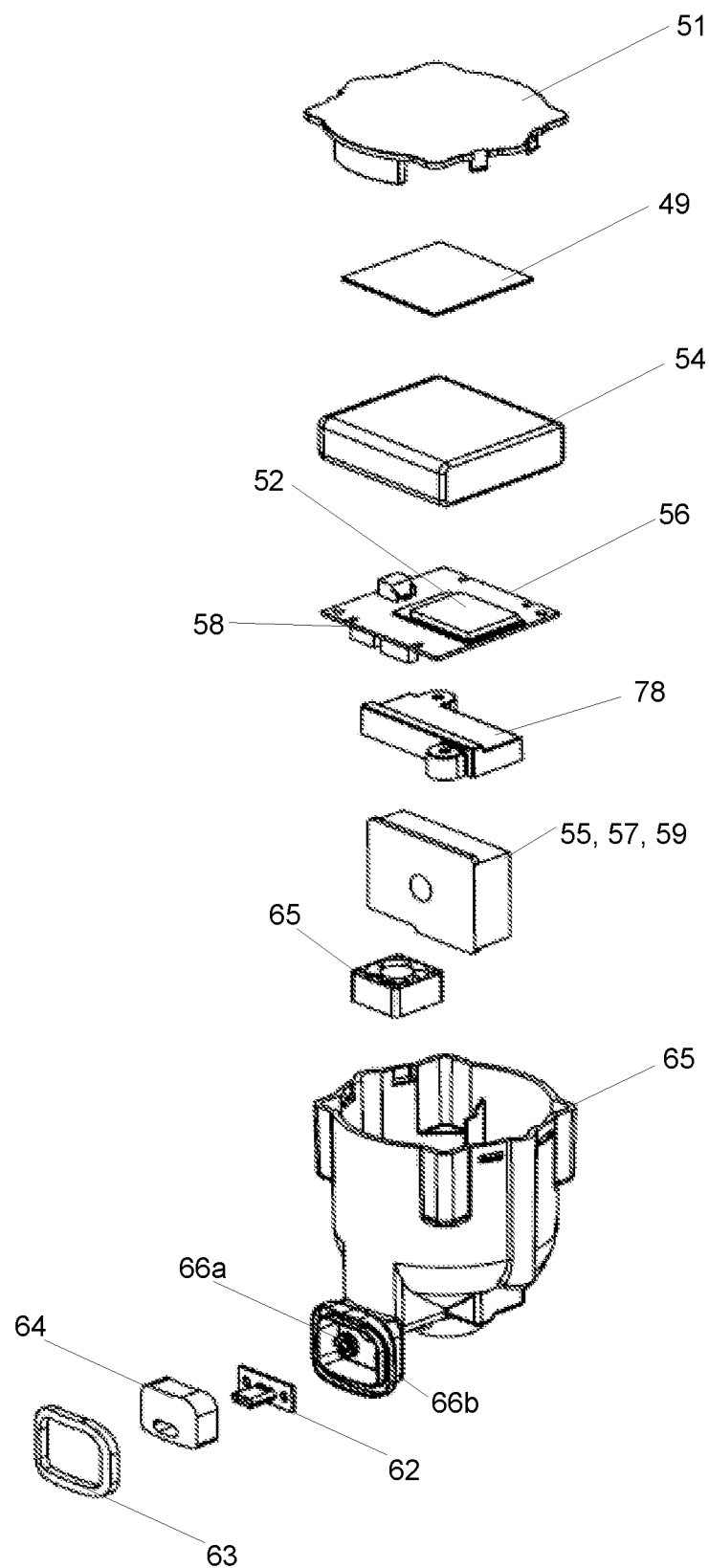
FIG. 9 is an exploded parts front perspective view illustrating the electronics housing.
Figure 10A:
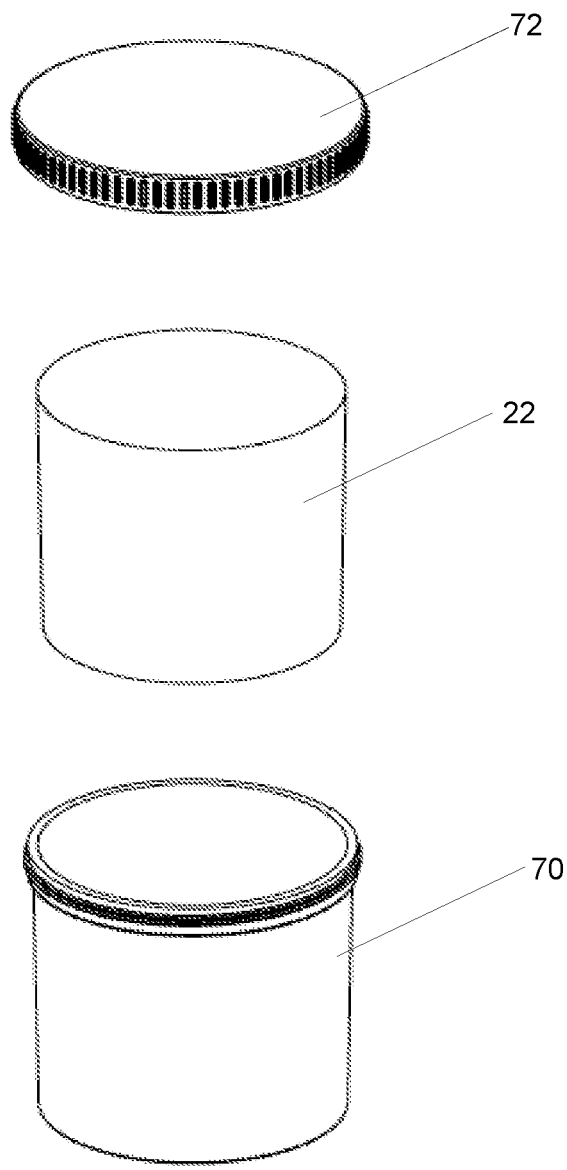
FIG. 10a is an exploded parts front perspective view illustrating the gel cartridge.
Figure 10B:
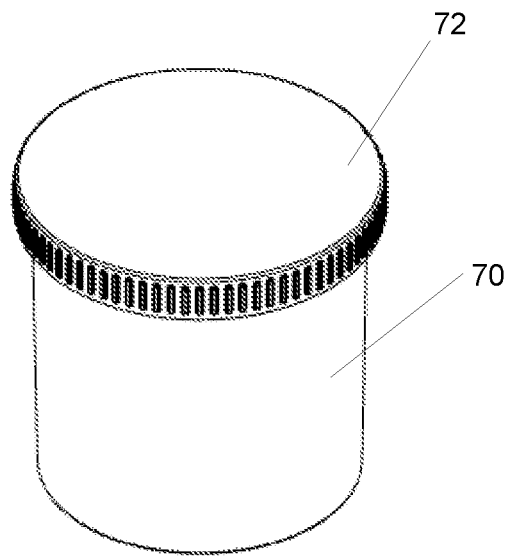
FIG. 10b is a front perspective view illustrating the gel cartridge.

Referring more specifically to FIGS. 10a and 10b, in this example, the composition 22 is preferably supplied as a gel within a replaceable cartridge 70 that is fitted, when installed, within the receptacle 26. The replaceable cartridge 70 has a removable lid 72 that is removed, and may be discarded, prior to the cartridge 70 being fitted to the receptacle 26. It is noted that the arrangement is such that a rim of the cartridge 70 remains below the apertures 36 on the neck 44 of the lid 40. The fill level of the gel is such that the headspace 41 is maintained above the gel. The apertures 36 are located about the sides of the headspace 41. However, it is noted that that replaceable cartridge 70 may also carry a liquid or viscous liquid. Other examples, may omit the cartridge 70 and, for example, a liquid or viscous liquid may be poured directly into the receptacle 26 and captured therein with the lid 40.

Turning to the evaporation rate for the vapour from the gel, the evaporation rate is believed to be firstly a function of the size of the apertures 36, which are relatively small, and secondly a function of fan speed. Temperature and humidity may also have a effect. Accordingly, the size of apertures 36 has been determined to be the primary control of the pre-determined rate of evaporation from the gel. Referring to Table 1 below, the size of the at least one aperture 36 is selected such that the pre-determined rate of the evaporable vapour is in range of about 0.5 to 2.0 grams per day, and preferably about 1 gram per day. It noted that 0.6 grams/day is deemed the minimum rate for biological efficacy.

In this example, twelve apertures each have a diameter of 2 mm are provided. The collective total size of the apertures 36 may be order of about 30 to 40 mm$^2$ such that, for example, an airflow about 1.5 to 2 m/s will release about 1 gram per day of the composition 22, as shown below in Table 1. A single slot aperture having a similar area may achieve a similar result. Accordingly, as will be further details below, the fan speed 18 may be used to control the amount of the composition 22 entrained in the emitted filtered air.

The airflow rate through the air passageway 24 is the range of about 4 to 8 litres per second. The air flow variation has an effect on the evaporation rate, being in the range of about 0.75 to 1.10 grams per day.

TABLE 1

Evaporation Rate from Gel based on Fan Speed. Apertures (12 by ϕ 2 mm) with 150 grams of Gel in Receptacle

| Voltage (V) | Airflow (m/s) | Airflow (L/S) | Evaporation Rate (g/day) |
|---|---|---|---|
| 3.5 | 1.26 | 4.85 | 0.75 |
| 4.5 (Typical) | 1.58 | 6.08 | 1.05 |
| 5.5 | 1.91 | 7.35 | 1.08 |

The quantity of the composition 22, namely the gel, may be about 150 grams within the canister 70. Accordingly, the lifespan of the gel at a rate of about 1 g/day (at a medium setting of 4.5V) is about 5 months or 150 days. Of course, the lifespan may vary depending on the evaporable component of the gel or nature of the composition 22.

Turning now to the fan 18 and filter 20, the fan 18 may be an electric axial fan arranged to rotate about a vertical axis of the housing 12. The air flow is therefore generally vertical between the inlet 14 and the outlet 16. In this example, the fan 18 is located between the lower void 34 in which the filter 20 is located and the upper receptacle 26 in which the composition 22 is located. The fan 18 is controlled by a controller 52 located in an inner electronics housing 53, shown best in FIG. 9, located between the fan 18 and the receptacle 26. The fan 18 is supported by a fan housing 19. The fan housing 19 also supports a power button PCB 69. The fan 18 may be a 50×50 mm package with nominal 5V supply.

The inner housing 53 is shaped to splay outwardly from the fan 18 to the annular portion 38 of the passageway. This shape assists to guide the airflow around the inner electronics housing 53 to minimise losses and associated noise. The inner housing 53 is sealed with a lid 51.

The inner housing 53 also houses further electronic components such as a battery 54 and sensors 55 that communicates with the controller 52 that is fitted to a main PCB 56. A battery mounting foam 49 is provided between the battery 54 and the lid 51.

A further PCB 56 having a communications module 58 is located at a side of the housing 12 adjacent an on/off switch 60 and a charging port 62 is provided on an opposing side of the housing 12. The sensors 55 are preferably a particle or dust sensor 57 and, in some examples, an additional dew point sensor 59. The particle sensor 57 may be configured to detect PM2.5 particulate matter (i.e. particles of 2.5μ size). The controller 52, battery 54, PCB 56, sensors 55, a memory device 61, a communications module 58, on/off switch 60 and a charging port 62 all form part of a control system 100 that is further described below.

It is noted that in this example conduits **64*a*, 64*b* are provided through the side wall 32 of housing 12 between the external environment and the particle sensor 57 within the inner housing 54. The inlet conduit 64*a* leads to an inlet port 66*a* via a mesh 64 that is sealed via a seal 63 to the side wall 32, and ultimately to the particle sensor 57. A particle sensor fan 65 is provided to draw air though the conduit 64*a* and exhaust the air via the port 66*b* and the exhaust conduit 64*b*. The particle sensor fan 65 is controlled controller 52. This allows the particle sensor 57 to sample the external air quality and provide a signal indicative of the air quality to the controller 52 based on the suspended particulate matter in the air. The controller 52 may activate the apparatus 10 or adjust the speed of the fan 18** based on the sampled air quality.

In this example, the filter 20 is preferably a HEPA filter through which air is drawn from the inlet 14 to an outer passage 77, through the filter 60 to an inside passage 71 and then into the fan 18. The filters 20 seals within the housing 12 to prevent bypass of airflow. A removable base cap 68 is provided at the base 28 of the housing 12 to enclose the lower void 34 that houses the filter 20. The base cap 68 may be removed to access and replace the filter 20. The HEPA filter may be capable of filtering up to 1.0μ particle size. The HEPA filter may in this example be 72 mm OD×84 mm high.

Turning now to the composition 22, the composition 22 is preferably an evaporable substance or substance that emits a volatile adapted to affect, reduce or kill air born pathological or biological material. An example of the composition 22 may be a gel insert, cartridge or disk that is impregnated with an essential oil. The essential oils that have been found to affect, reduce or kill mold are, for example, clove oil, cinnamon, peppermint, rosemary, eucalypt oils have also been found affect against mold and bacteria. Accordingly, a gel with a blend of clove oil, rosemary and eucalyptus extracts may be used. A gel quantity of about 150 to 200 grams may initially be provided. An example gel may include a polysaccharide gelling agent, or in other examples, a simple gelatin gelling agent. The gelling agent being formed with the blend evaporable oils.

Referring now to FIG. 14, the apparatus 10 may be provided as part the system 100 for air cleaning and sanitising indoor air. The apparatus 10 includes control and sensor components 106 including the controller 52 of the apparatus 10 may communicate, using the communication module 58, directly or indirectly via a network 102 with a remote computing device 104 that may be a smart phone, tablet or the like. The computing device 104 may include and operate application software in communication with a remote server (not shown) that allows the computing device 104 to communicate with and operate the apparatus 10. The communications module 58 may include WiFi™ and or Bluetooth™ functionality to allow communication with the computing device 104.

The computing device 104 may be used to configure the controller 52 to automatic modes of operations such as operating times (i.e. timer or on/off timer), speeds and modes. The controller 52 may also be configured to send messages or alerts to the computing device 104 under predetermined conditions. For example, if the sensors 55 determine a poor air quality reading—the controller 52 may send an alert to the computing device 104 to prompt the user to turn on the apparatus 10. In some examples, a real-time air quality reading may be provided and these readings may be stored on the memory device 59. Historical data may then be stored and later viewed by the computing device 104. The control system 100 may also allow pluralities of the apparatuses 10 to be controlled via a single computing device 104, and comparable air quality readings and status to be display for each operable apparatus 10.

In some examples, the controller 52 may be configured to automatically activate the fan 18 of the apparatus if detects particles and the dew point exceeds a predetermined threshold. In other examples, the controller 52 may be configured to increase the speed of the fan 18 in response to an elevated air quality reading, such as high particulate matter. The increase fan speed functions to increase the local filtration and also increase the entrainment rate of the composition 22.

In a more specific example relating to the dew point sensor 59—this is a combined temperature and humidity sensor to track conditions throughout the day & night where mould spores may be released. Scientific data 'look up' charts may be provided and checked against actual readings. Dew point is a function of temperature and relative humidity and, for example, at 20 degrees centigrade at 50% relative humidity, the dew point is about 9 degrees. Mould may start to grow at room humidity of 80%. This means that in the given example, mould may start to grow at a surface temperature of about 13 degrees or less on the walls. Accordingly, for example, a trigger or alert for mould may be when the dew point is about 13 degrees. However, other trigger points for the dew point may be selected, as required.

Should conditions for mould spore release occur, the user will be alerted and/or the apparatus 10 may automatically switch on the fan 19 (depending on user settings). The hardware for the sensor 59 could be either an off-the-shelf dew point sensor, or individual temperature/humidity sensors—whichever is deemed suitable.

Further functionality of the system 100 may include one or more of; on/off control; fan speed control—low, medium, high settings. The medium setting will be about 1 to 1.5 m/s; View graph/data of particle count (live data and historical data); Compare particle count data against approved levels of particulates and provide graphical feedback; Air quality range to be good, moderate, poor and very poor. Acceptable levels of pm2.5 will differ for each country. A country setting may be required in the application software which will adjust the "good-very poor" range to suit the local policy.

The application software may be configured to: view graph/data of dew point (temperature & humidity); and live data and historical data; compare dew point data against scientific thresholds and provide graphical feedback (green/red etc.); provide feedback to determine when the HEPA filter need changing or the pre-filter requires cleaning; provide feedback with when the composition/gel requires changing; auto mode, to switch on/off with a timer; set-up mode/settings page; HEPA & gel cartridges will be required to be changed over the course of a year; and as part of the application software, there may be a setting to allow users to automatically order consumables such as the filter. The air quality via the dust sensor 57 may be configured to be sampled at regular intervals, for example every 5 or 10 seconds, or every 60 seconds. This requires selective operation of the dust sensor 57 and the dust sensor fan 65 by the controller 52.

The software of the system 100 may include algorithms which extrapolate Fan Speed and time of use, to determine the approximate life of both the HEPA filter and composition/gel cartridge. Accordingly, methods performed by the system 100 including the apparatus 10 and device 104 may include various maintenance type routines. For example, the software application may determine when HEPA filter or composition requires changing and alerts the user. For example, the controller 52 or the remote device 104 may time the on-time of the fan 18 and provide an alert when a pre-determined number of hours have passed therefore being indicative of the life of the HEPA filter. The user may need to reset the time counter through the application software of the remote device 104, once they have changed either HEPA filter or composition.

In addition to warnings through the application software, the on/off button 60 of apparatus 10 is also configured to change colour to indicate various statuses of the apparatus 10. For example, the on/off button 60 may be configured as follows: White LED=Apparatus 10 is switched on, Solid Orange LED=HEPA filter requires changing (or pre-filter washing), Blinking Orange LED=Gel/composition requires changing, Red LED=Both HEPA and Gel/composition require changing. The on/off button 60 may be be a non-latched push-push micro-switch. It may require a multi-colour LED which is used as a maintenance indicator.

The system 100 may be configured to operate in an access point method and/or Internet (client) mode. Access point method will be a direct WiFi connection between the apparatus 10 and the smart device 104. The apparatus 10 will act as the network host and the smart device 104 will connect to the SSID of the apparatus 10 using a factory set password (which can later be changed via an application of application software operated by the smart device 104. While in this mode, the application software will only allow simple functions: a. Setting of the home/office WiFi router credentials; b. Turning apparatus 10 ON or OFF c. Changing the user settings of the device such as fan speed, timer, LED colour etc. d. Real-time reading of the air quality.

In the Internet (client) mode, the apparatus 10 has connected online using the SSID and credentials of the local WiFi hotspot (e.g. at home or office). These credentials would have been set up earlier when the device was in Access Point Mode. While in this mode, the apparatus 10 will log onto a cloud hosted web service on a server (not shown) of the system 100 where it can be uniquely identified and its functions are made available over this service. The cloud hosted web service may allow multiples of the apparatus 10 to be simultaneously connected and controlled by a user. For example, multiples of the apparatus 10 may provide dust and dew point readings at different locations within a dwelling or multiple dwellings. The cloud hosted web service may also allow related apparatuses 10, such as those owned by friends, connected and share data such as air quality data. The cloud hosted web services may also allow full remote control of one or more of the apparatuses 10.

In the Internet (client) mode, the device now provides full functionality. These include all functions present in Access Point Mode as well as other internet enabled functions: a. Automatic resetting of the local device clock to internet time; b. Ability to upload locally stored data related to air quality and usage; c. Ability to be connected to a group of units at a home or office setting. For example, the user is able to allocate names to units such as 'Master Bedroom', 'Living Room' etc. d. Set up of timed ON/OFF functions. e. Reporting of trend data from the cloud.

In relation the application software operated by the device, the functions of the software may further include: On/off control; Fan Speed control will use a sliding 1-5 scale; View graph/data of particle count. Live data and historical data; Compare particle count data against approved levels of particulates and provide graphical feedback. Air quality range to be Good, Moderate, Poor and Very Poor. Acceptable levels of PM2.5 will differ for each country; View graph/data of dew point (temperature & humidity). Live data and historical data; Compare dew point data against scientific thresholds and provide graphical feedback (green/red etc.); Provide feedback to determine when the HEPA filter need changing or the pre-filter requires cleaning; Provide feedback with when the gel requires changing; Auto Mode, to switch on/off with a timer; Set-up mode/settings page; HEPA & Gel cartridges will be required to be changed over the course of a year. As part of the application, there may be a setting to allow customers to automatically order consumables; Outdoor PM2.5 readings to be displayed next to Indoor PM2.5 levels; The application software may be configured to allow consumers to connect to friends who also use apparatus 10 and review their friends indoor & outdoor PM2.5 levels. To enable this feature, friends will need to request an invitation to join their network and accept this invitation. Users may also be able to remove a friend.

Turning now to a method of use, once configured, a method for air filtering and sanitising air may include drawing air through the housing 12 using the fan 18 such that air is passed between the inlet 14 and the outlet 16 of the housing 12. Filtering the air using the filter 20 arranged between inlet 14 and the outlet 16 to provide filtered outlet air; Sanitising or treating the filtered air proximate the outlet 16 by communicating the filtered air with a receptacle 26 containing the composition 22 such that a portion of the composition 22 is entrained into the filtered outlet air.

The method of use may also include measuring an air quality parameter such as suspended particles, dew point or humidity, and at least one of activating and altering the fan speed based on the measured air quality parameter. The altering of the fan speed increasing the filtering and also increasing the entrainment rate (grams/day) of the composition 22. In some examples, the method may also include the measuring of an air quality parameter and providing an air quality alert such as an alert message to the computing device 104. Various further methods of operation such as recording, alerts and apparatus management methods such as filter and composition replacement indicators are also contemplated herein. The method may include activating RGB lights 21 of the light ring 23 in a colour or colour sequence reflective of the quality of the air, for example, an amber or red light sequence indicating a high level of dust or particles in the air.

Advantageously, there has been described an apparatus, system and method for cleaning or treating indoor air. In particular, the apparatus is configured to firstly filter air and then communicate the filtered air with a composition that is adapted to effect, reduce or kill airborne biological or material such as mould, bacteria, fungus and the like.

The arrangement is such that apertures of the receptacle provide slow release of the composition into the emitted airflow. The release rate may be increased and decreased based on the fan speed, although the small aperture size assists to keep the release rate relatively small and within a pre-determined range. The apparatus may be stand alone having an internal controller or in communication with an external device such as a smart phone to allow alerts such as air quality alerts to be provided to the user and allow the user to remotely configure and control the apparatus.

Further advantageously, the apparatus has a removable lid to allow easy replacement of the cartridge that carries the composition, and a removable base to allow easy replacement of the filter. The internal controller or external device may be configured to alert a user to change the cartridge or filter. Further still the apparatus may communicate with a remote device that allows tracking of the air quality, air quality alerts, configuration of the apparatus and control over the apparatus.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any known matter or any prior publication is not, and should not be taken to be, an acknowledgment or admission or suggestion that the known matter or prior art publication forms part of the common general knowledge in the field to which this specification relates.

While specific examples of the invention have been described, it will be understood that the invention extends to alternative combinations of the features disclosed or evident from the disclosure provided herein.

Many and various modifications will be apparent to those skilled in the art without departing from the scope of the invention disclosed or evident from the disclosure provided herein.

The claims defining the Invention are as follows:

1. An air filtering and treatment apparatus, the apparatus including:

a housing having an air inlet, an air outlet, an air passageway between the inlet and outlet, and a fan arranged to urge air through the air passageway between the air inlet and the air outlet, wherein the housing includes a filter arranged to filter air passing through the air passageway, and a receptacle located toward the air outlet relative to the filter, wherein the receptacle is adapted to hold treatment composition such that an evaporable vapour associated with the treatment composition is able to accumulate in a headspace of the receptacle, the receptacle including at least one aperture located at a side thereof laterally of the headspace and in fluid communication with the headspace, and wherein at least a portion of the air passageway is shaped such that air flows substantially perpendicularly past the at least one aperture of the receptacle such that a predetermined amount of the evaporable vapour from the headspace is entrained into the filtered air released from the air outlet;

wherein the receptacle includes a lid removeably securable thereto, and wherein the lid includes a head and a neck, and wherein the neck provides the side of the receptacle and includes the at least one aperture, the head including a radial lip extending at least partially over the air outlet so as to outwardly deflect airflow.

2. The apparatus according to claim 1, wherein the receptacle is adapted to receive a removable cartridge containing the treatment composition, the cartridge having an openable top so as to allow fluid communication between the treatment composition and the least one aperture, the lid being securable over the removable cartridge.

3. The apparatus according to claim 1, wherein the radial lip is located immediately above the at least one aperture, and wherein the at least one aperture is located at the air outlet.

4. The apparatus according to claim 3, wherein the portion of the air passageway is arranged to be normally vertically oriented.

5. The apparatus according to claim 1, wherein the at least one aperture substantially skirts the side of the receptacle.

6. The apparatus according to claim 1, wherein the at least one aperture is provided in the form of a plurality of spaced apart apertures substantially skirting the side of the receptacle.

7. The apparatus according to claim 6, wherein the portion of the air passageway substantially skirts the receptacle.

8. The apparatus according to claim 1, wherein the at least one aperture is provided in the form of a plurality of radially arranged apertures spaced apart and substantially skirting the side of the receptacle, and wherein the portion of the air passageway is annular in shape and substantially skirts the plurality of radially arranged apertures.

9. The apparatus according to claim 1, wherein the at least one aperture is arranged at the air outlet.

10. The apparatus according to claim 1, wherein a size of the at least one aperture is selected such that the pre-determined amount of the evaporable vapour is in range of 0.5 to 2.5 grams per day.

11. The apparatus according to claim 10, wherein a size of the at least one aperture is selected such that the pre-determined amount of the evaporable vapour is 1 gram per day.

12. The apparatus according to claim 1, wherein a size of the at least one aperture is selected such that the pre-determined amount of the evaporable vapour is in range of 0.5 to 2.5 grams per day with an airflow rate through the air passageway in the range of 4 to 8 litres per second.

13. The apparatus according to claim 1, wherein the housing includes a base and a top, and wherein the air inlet is located toward the base and the air outlet is located toward the top.

14. The apparatus according to claim 13, wherein the at least one aperture is provided in the form of a plurality of apertures arranged toward a top of the receptacle, the plurality of apertures being arranged perpendicular to the direction of the air directed by the portion of the air passageway.

15. The apparatus according to claim 14, wherein the portion of the passageway is annular in shape being defined between an outer wall of the housing and the receptacle.

16. An air filtering and treatment apparatus, the apparatus including:
a housing having an air inlet, an air outlet, an air passageway between the inlet and outlet, and a fan arranged to urge air through the air passageway between the air inlet and the air outlet,
wherein the housing includes a filter arranged to filter air passing through the air passageway, and a receptacle located toward the air outlet relative to the filter,
wherein the filter is removable to allow changing of the filter,
wherein the receptacle includes a removeable lid so as to be adapted to receive a removable cartridge containing a treatment composition, the lid including at least one aperture adapted to communicate a vapour associated with the treatment composition with filtered air such that emitted air contains a pre-determined amount of the vapour, and
wherein the lid includes a head and a neck, and wherein the neck provides the at least one aperture, and the head includes a radial lip extending at least partially over the air outlet so as to outwardly deflect airflow.

17. An air filtering and treatment apparatus, the apparatus including:
a housing having an air inlet toward a base thereof, an air outlet toward to top thereof, an air passageway between the air inlet and air outlet, a fan arranged to urge air through the air passageway between the air inlet and the air outlet, a filter, a receptacle and an inner electronics housing,
wherein the filter is arranged toward the base to filter air drawn by the fan from the air inlet, the receptacle is located toward the air outlet relative to the filter and the inner electronics housing is located substantially intermediate the filter and the receptacle along with the fan, the inner electronics housing being shaped to direct air from the filter into a portion of the air passageway substantially about inner electronics housing and the receptacle toward the air outlet,
wherein the base is removable to allow changing of the filter, and wherein the receptacle includes a removable lid to allowing receipt of a treatment composition into the receptacle such that an evaporable vapour associated with the treatment composition is releasable via at least one aperture at a side of the receptacle into the filtered air of the portion of the air passageway, and
wherein the lid includes a head and a neck, and wherein the neck provides at the least one aperture at the side of the receptacle, and the head includes a radial lip extending at least partially over the air outlet so as to outwardly deflect airflow.

* * * * *